United States Patent
Li et al.

(10) Patent No.: US 10,012,869 B2
(45) Date of Patent: Jul. 3, 2018

(54) METHOD AND DEVICE FOR DETECTING RUBBING CLOTH

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Jian Li, Beijing (CN); Yan Yang, Beijing (CN); Shichao Wang, Beijing (CN); Yuguang Fan, Beijing (CN); Jingpeng Li, Beijing (CN); Yuekai Gao, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/542,335

(22) PCT Filed: Jun. 3, 2016

(86) PCT No.: PCT/CN2016/084706
§ 371 (c)(1),
(2) Date: Jul. 7, 2017

(87) PCT Pub. No.: WO2017/148032
PCT Pub. Date: Sep. 8, 2017

(65) Prior Publication Data
US 2018/0046036 A1    Feb. 15, 2018

(30) Foreign Application Priority Data
Mar. 4, 2016   (CN) .......................... 2016 1 0124429

(51) Int. Cl.
*G01L 5/00*      (2006.01)
*G02F 1/1337*    (2006.01)
(Continued)

(52) U.S. Cl.
CPC ....... *G02F 1/133784* (2013.01); *G01N 21/95* (2013.01); *G02F 1/1309* (2013.01);
(Continued)

(58) Field of Classification Search
CPC ............. G02F 1/133784; G02F 1/1309; G02F 1/133516; G02F 1/133723; G01N 2021/9513
(Continued)

(56) References Cited

U.S. PATENT DOCUMENTS

2006/0171727 A1* 8/2006 Inui .................... G03G 15/1605
399/27
2007/0289608 A1* 12/2007 Choi ........................ B08B 5/02
134/21
(Continued)

FOREIGN PATENT DOCUMENTS

CN    102707497 A    10/2012
CN    203673187 U    6/2014
(Continued)

OTHER PUBLICATIONS

International Search Report and Written Opinion for International Application No. PCT/CN2016/084706, dated Nov. 30, 2016.

*Primary Examiner* — Max Noori
(74) *Attorney, Agent, or Firm* — Calfee, Halter & Griswold LLP

(57) ABSTRACT

A method and a device for detecting a rubbing cloth, the method includes rubbing a coloring sheet with the rubbing cloth; and detecting the rubbing cloth according to a pattern in a rubbed region. The device includes a base platform, a (Continued)

coloring sheet is provided on the base platform; and a rubbing roller, a rubbing cloth to be detected is provided on an outer surface of the rubbing roller, the rubbing roller is disposed in parallel to the base platform and the rubbing roller is configured to rub on the coloring sheet. By coloring the rubbing cloth with the coloring sheet, and detecting the rubbing cloth with a pattern in a rubbed region, the quality of the rubbing cloth can be detected by observing the depth and the arrangement of the pattern.

18 Claims, 5 Drawing Sheets

(51) Int. Cl.
*G01N 21/95* (2006.01)
*G02F 1/13* (2006.01)
*G02F 1/1335* (2006.01)
(52) U.S. Cl.
CPC .. *G02F 1/133516* (2013.01); *G02F 1/133723* (2013.01); *G01N 2021/9513* (2013.01)

(58) Field of Classification Search
USPC ........................................... 73/862.55
See application file for complete search history.

(56) References Cited

U.S. PATENT DOCUMENTS

| 2014/0083205 | A1* | 3/2014 | Hu | G02F 1/1337 73/862.55 |
| 2016/0327833 | A1* | 11/2016 | Zhan | G02F 1/133784 |
| 2017/0023812 | A1* | 1/2017 | Jing | G02F 1/1303 |

FOREIGN PATENT DOCUMENTS

| CN | 104808394 A | 7/2015 |
| CN | 105334674 A | 2/2016 |
| CN | 105549271 A | 5/2016 |
| JP | 2001021893 A | 1/2001 |
| KR | 20130057739 | 6/2013 |

* cited by examiner

METHOD AND DEVICE FOR DETECTING RUBBING CLOTH

CROSS-REFERENCE TO RELATED APPLICATIONS

The present application is based on International Application No. PCT/CN2016/084706, filed on Jun. 3, 2016, which is based upon and claims priority to Chinese Patent Application No. 201610124429.0, filed on Mar. 4, 2016, and the entire contents thereof are incorporated herein by reference.

TECHNICAL FIELD

The present disclosure relates to the field of detection technology, and more particularly, to a method and a device for detecting a rubbing cloth.

BACKGROUND

In liquid crystal displays, in order to arrange liquid crystal molecules regularly, it is necessary to provide an alignment film. At present, alignment films are mostly produced by a rubbing method. In the rubbing method, a rubbing cloth is placed on a rubbing roller of an alignment processing device, and a series of small grooves regularly arranged toward a particular direction on a PI (Polyimide) film are produced using fluffs of the rubbing cloth. If the quality of the rubbing cloth is defective, it will lead to formation of irregularly arranged grooves or traces on the surface of the produced PI film, thus affecting the regular arrangement of liquid crystal molecules, and ultimately leading to display defects in the liquid crystal display and low yield of products. Therefore, the quality of the rubbing cloth directly affects the quality of the alignment film.

After the rubbing cloth is placed on the rubbing roller, detection is performed on the rubbing cloth before put it into operation. At present, a conventional detection method is to coat a PI film on a glass substrate specifically designed for the detection, and to rub the PI film with the rubbing cloth on the rubbing roller and perform a rubbing alignment process. Then, the processed glass substrate is subjected to water vapor spraying and light irradiation, and the quality of the rubbing cloth is judged by an engineer on the basis of the traces on the PI film. In practice, it is required to remove the coated PI film the glass substrate for detection after each test, and then put the glass substrate into operation again. It will occur a quality defect which disturbs the judgment of the engineer on the glass substrate after it is repeatedly utilized. So this method fails to effectively detect the quality of the rubbing cloth. In addition, the cost of the detection method is high.

It should be noted that, information disclosed in the above background portion is provided only for better understanding of the background of the present disclosure, and thus it may contain information that does not form the prior art known by those ordinary skilled in the art.

SUMMARY

Embodiments of the present disclosure provides a method and a device for detecting a rubbing cloth.

According to one aspect, an embodiment of the present disclosure provides a method for detecting a rubbing cloth, wherein the method includes following steps: rubbing a coloring sheet with the rubbing cloth; and detecting the rubbing cloth according to a pattern in a rubbed region.

In some embodiments, the step of detecting the rubbing cloth according to a pattern in a rubbed region includes: detecting the rubbing cloth by detecting a pattern on the coloring sheet after the coloring sheet is rubbed.

In some other embodiments, the step of detecting the rubbing cloth according to a pattern in a rubbed region includes: rubbing a to-be-colored sheet with a colored rubbing cloth; and detecting the rubbing cloth by detecting a pattern formed on the to-be-colored sheet after the to-be-colored sheet is rubbed by the rubbing cloth.

In some other embodiments, the coloring sheet is rubbed with at least part of the region other than the region for rubbing alignment operation on the rubbing cloth.

In some other embodiments, the step of rubbing a coloring sheet with the rubbing cloth includes: providing a coloring sheet on a base platform; attaching the rubbing cloth on a rubbing roller; and rubbing the coloring sheet with a rolling action of the rubbing roller.

In some other embodiments, the step of rubbing the coloring sheet with a rolling action of the rubbing roller includes: rubbing a plurality of coloring sheets with the rubbing cloth; wherein the plurality of coloring sheets are disposed side by side along a direction perpendicular to a rubbing direction of the rubbing cloth, and the plurality of coloring sheets are disposed at different heights in a direction perpendicular to the surface of the base platform.

In some other embodiments, prior to the step of rubbing the coloring sheet with a rolling action of the rubbing roller, the method also includes: providing a substrate for detection on the base platform; and perform a preliminary rubbing process on the substrate for detection with the rubbing cloth.

In some other embodiments, the step of rubbing a to-be-colored sheet with a colored rubbing cloth includes: providing the to-be-colored sheet downstream of the coloring sheet along a rubbing direction of the rubbing cloth; and immediately after the coloring sheet is rubbed with the rubbing cloth, rubbing the to-be-colored sheet.

In some other embodiments, the step of rubbing the coloring sheet with a rolling action of the rubbing roller includes: rolling the rubbing cloth on the plurality of coloring sheets; wherein the plurality of coloring sheets are disposed side by side along a direction perpendicular to a rubbing direction of the rubbing cloth, and the plurality of coloring sheets are disposed at different heights in a direction perpendicular to a surface of the base platform; and the step of providing the to-be-colored sheet downstream of the coloring sheet along a rubbing direction of the rubbing cloth includes: a plurality of to-be-colored sheets are disposed side by side in the direction perpendicular to the rubbing direction of the rubbing cloth, wherein the plurality of to-be-colored sheets are disposed at different heights in the direction perpendicular to a surface of the base platform.

In some other embodiments, the plurality of to-be-colored sheets are disposed corresponding to the plurality of coloring sheets one by one, and a pair of corresponding to-be-colored sheet and coloring sheet are disposed at the same height.

In some other embodiments, a plurality of carrier sheets with different thicknesses are employed to bear the coloring sheets, to dispose the plurality of coloring sheets at different heights.

In some other embodiments, a plurality of carrier sheets with different thicknesses are employed to bear the coloring sheets and the to-be-colored sheets, to dispose the plurality of coloring sheets at different heights.

According to another aspect, an embodiment of the present disclosure provides a device for detecting a rubbing cloth, wherein the device includes: a base platform, a coloring sheet is provided on the base platform; and a rubbing roller, a rubbing cloth to be detected is provided on an outer surface of the rubbing roller, the rubbing roller is disposed in parallel to the base platform and the rubbing roller is configured to rub on the coloring sheet.

In some other embodiments, the device further includes a first carrier sheet disposed corresponding to at least part of the region other than the region for rubbing alignment operation on the rubbing cloth, and the coloring sheet is disposed on the first carrier sheet.

In some other embodiments, the device includes a plurality of said first carrier sheets, the plurality of said first carrier sheets are disposed side by side in a direction perpendicular to a rubbing direction of the rubbing cloth, and the plurality of said first carrier sheets have different thicknesses, and the plurality of said first carrier sheets are configured to bear the coloring sheets respectively.

In some other embodiments, the device further includes: a to-be-colored sheet disposed on the base platform, the to-be-colored sheet is disposed downstream of the coloring sheet along a rubbing direction of the rubbing cloth, to accept the rubbing of the rubbing cloth after the rubbing cloth is colored.

In some other embodiments, the device further includes a plurality of second carrier sheets configured to bear the to-be-colored sheets, the plurality of second carrier sheets are disposed downstream of the first carrier sheets along the rubbing direction of the rubbing cloth, and corresponding to the plurality of first carrier sheets one by one, and a pair of corresponding first carrier sheet and second carrier sheet have the same thickness.

In some other embodiments, a stopper structure is provided on the base plat form and configured to limit positions of the first carrier sheets and the second carrier sheets.

In some other embodiments, the device further includes a rotary disc rotatably provided on the base platform, wherein the coloring sheet is disposed on the rotary disc, the device further includes a to-be-colored sheet disposed on the rotary disc, and the coloring sheet and the to-be-colored sheet are disposed spaced apart along the circumferential direction of the rotary disc.

According to another aspect, an embodiment of the present disclosure provides a device for manufacturing an alignment film, including: a base platform; and a rubbing roller, a rubbing cloth is provided on an outer surface of the rubbing roller, the rubbing roller is disposed in parallel to the base platform, wherein a processing region configured to position a substrate with a film to be processed and a detection region configured to detect a rubbing cloth are provided on the base platform, a coloring sheet is placed on the detection region; and the rubbing roller is configured to rub the coloring sheet while processing the substrate with a film to be processed.

BRIEF DESCRIPTION OF THE DRAWINGS

In order to more clearly illustrate the technical solutions in embodiments of the present disclosure, drawings to be used in the description of the embodiments will be briefly introduced below. Apparently, the drawings in the following description are only for some embodiments of the present disclosure, and other drawings may be obtained based on these drawings by those skilled in the art without paying creative effort.

DETAILED DESCRIPTION

In order to make the objective, technical solutions and advantages of the present disclosure to be more apparent, hereinafter, the embodiments of the present disclosure will be described in detail, in combination with the drawings.

Figure 1:
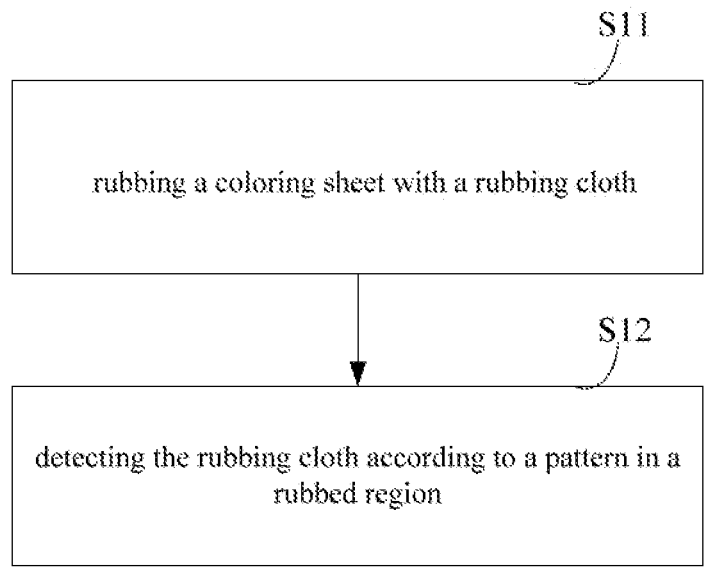
FIG. 1 is a flow chart of a method for detecting a rubbing cloth provided by an embodiment of the present disclosure.

FIG. 1 is a flow chart of a method for detecting a rubbing cloth provided by an embodiment of the present disclosure. As shown in FIG. 1, the method includes: S11: rubbing a coloring sheet with a rubbing cloth; S12: detecting the rubbing cloth according to patterns in a rubbed region. In this method, by detecting according to the pattern in the rubbed region, it can eliminate the need for a substrate and a PI film as required by detection in the related art, which will significantly reduce the detection cost, and can achieve an intuitive detection effect. In a particular example, the patterns in the rubbed region include a pattern of the coloring sheet which is rubbed and a pattern of the rubbing cloth which is colored by the coloring sheet.

Figure 2:
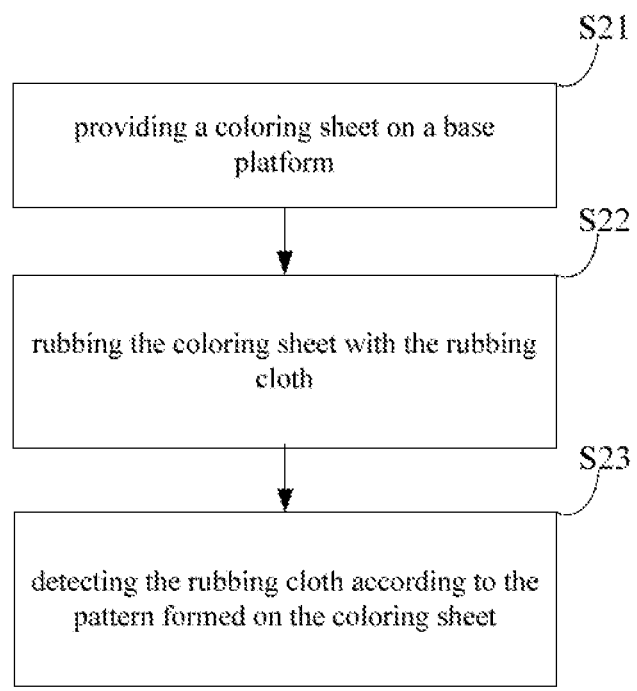
FIG. 2 is a flow chart of a detailed method for detecting a rubbing cloth provided by an embodiment of the present disclosure.

FIG. 2 is a flow chart of a detailed method for detecting a rubbing cloth provided by an embodiment of the present disclosure. In the embodiment as shown in FIG. 2, the rubbing cloth is detected according to the pattern formed on the coloring sheet. As shown in FIG. 2, the method includes the following steps S21, S22 and S23.

S21: providing a coloring sheet on a base platform. A processing region configured to position a substrate with a film to be processed and a detection region configured to detect the rubbing cloth are provided on the base platform, the coloring sheet is placed on the detection region.

Preferably, the coloring sheet is provided corresponding to at least part of a region other than the region which will be used for a rubbing alignment operation on the rubbing cloth. Thus, the rubbing alignment process and the detection process may be performed simultaneously. It should be noted that, all or part of the region other than the region which will be used for a rubbing alignment operation on the rubbing cloth may be colored. In addition, the substrate is the substrate used for processing the alignment film. After the processing, regularly arranged small grooves are formed on the surface of the alignment film, which facilitates regular arrangement of the liquid crystal molecules.

S22: rubbing the coloring sheet with the rubbing cloth.

By rubbing the coloring sheet with the rubbing cloth, a pattern is formed on the surface of the coloring sheet due to loss of pigment particles, while the pigment particles lost from the coloring sheet are attached to the rubbing cloth, to color the at least part of the region of the rubbing cloth.

Moreover, since the coloring sheet is preferably provided corresponding to at least part of a region other than the region which will be used for the rubbing alignment operation on the rubbing cloth, it can prevent region of the rubbing cloth which corresponds to the substrate from being contaminated by the coloring sheet.

In a specific embodiment, the rubbing cloth may be provided on the rubbing roller, and by rolling the rubbing roller, the coloring sheet is rubbed by the rubbing cloth, which can facilitate the operation.

Optionally, prior to the step S21, the method may also include: attaching the rubbing cloth on the rubbing roller, and then suspending the rubbing roller inside an alignment processing device.

In an implementation, double-sided adhesive may be used for adhering the rubbing cloth on the rubbing roller.

Further, optionally, prior to attaching the rubbing cloth on the rubbing roller, the rubbing cloth is subject to preliminary detection. Only after the rubbing cloth is qualified in the preliminary detection, the rubbing cloth can be attached on the rubbing roller for further detection. The rubbing cloth being qualified in the preliminary detection means that the rubbing cloth does not have obvious appearance defects under visual detection of technical staff.

S23: detecting the rubbing cloth according to the pattern formed on the coloring sheet.

In the embodiment of the present disclosure, by coloring at least part of a region other than the region which will be used for a rubbing alignment operation on the rubbing cloth, it can prevent the region where the substrate is located from being contaminated by the pigment. Moreover, the rubbing cloth is detected according to the pattern of the colored region, and the quality of the rubbing cloth can be detected by observing the depth and the arrangement of the pattern. The rubbing cloth is detected according to the pattern formed on the surface of the coloring sheet due to loss of pigment particles, the pattern is intuitive and thus the detection result is more accurate.

It should be noted that, in the embodiment of the present disclosure, the coloring sheet may refer to carbon paper which is readily available and inexpensive, which can reduce the detection cost.

Optionally, one or more coloring sheets may be provided. When a plurality of coloring sheets are provided, the plurality of coloring sheets are side by side in a direction perpendicular to the rubbing direction of the rubbing cloth, and the plurality of coloring sheets are placed at different heights in a direction perpendicular to the surface of the base platform.

By placing a plurality of coloring sheets at different heights in a direction perpendicular to the surface of the base platform, a plurality of different patterns may be obtained. The indentation amount of the rubbing cloth used to produce a most desired pattern may be determined according to the different patterns, so that subsequent process parameters can be adjusted.

It should be noted that, the plurality of coloring sheets may be side by side in a direction perpendicular to the rubbing direction of the rubbing cloth, or may be spaced apart. Moreover, it is not necessary that the plurality of coloring sheets are arranged in one straight line. However, it should be avoided that coloring sheets overlaps with each other in the rolling and rubbing direction of the rubbing roller, to ensure that the one region of the rubbing cloth is colored only by one coloring sheet.

In an implementation, hard plastic sheets (used as carrier sheets) with different thicknesses may be placed under the plurality of different coloring sheets, such that the coloring sheets are placed at different heights in the direction perpendicular to the surface of the base platform.

Figure 3:
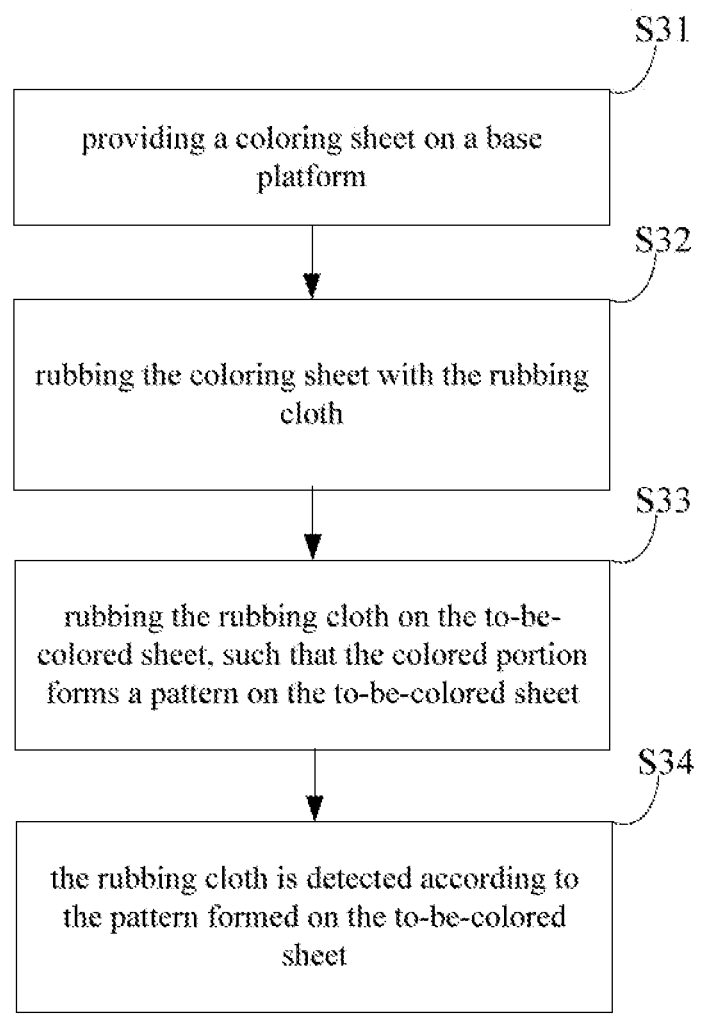
FIG. 3 is a flow chart of another detailed method for detecting a rubbing cloth provided by an embodiment of the present disclosure.

FIG. 3 is a flow chart of another detailed method for detecting a rubbing cloth provided by an embodiment of the present disclosure. In the embodiment as shown in FIG. 3, the rubbing cloth is detected according to a pattern formed on a to-be-colored sheet. As shown in FIG. 3, the method includes the following steps S31, S32, S33 and S34.

S31: providing a coloring sheet on a base platform.

Preferably, the coloring sheet is provided aligning with at least part of a region other than the region which will be used for the rubbing alignment operation on the rubbing cloth.

S32: rubbing the coloring sheet with the rubbing cloth.

S33: rubbing the to-be-colored sheet with the rubbing cloth, such that the colored portion of the rubbing cloth forms a pattern on the to-be-colored sheet.

By rolling the rubbing cloth on the to-be-colored sheet, pigment particles are left on the to-be-colored sheet to form a pattern.

S34: the rubbing cloth is detected according to the pattern formed on the to-be-colored sheet.

By performing rubbing alignment operation on the coloring sheet with the rubbing cloth to be detected, part of the pigment particles on the coloring sheet are attached on the rubbing cloth, then performing rubbing alignment operation on the to-be-colored sheet, such that the pigment particles on the rubbing cloth leave corresponding traces on the to-be-colored sheet to form a pattern, and the pattern formed on the to-be-colored sheet may be used to detect the rubbing cloth more accurately.

It should be noted that, preferably, the to-be-colored sheet mentioned in the embodiments of the present disclosure may be white paper, or may be other paper with an original color different from that of the pigment particle. This can increase the contrast of the pigment particle and the original color of the to-be-colored sheet, which make the pattern more apparent and the detection more accurate.

In an implementation of the present embodiment, one coloring sheet may be provided, and a plurality of to-be-colored sheets may be provided, and the area of the coloring sheet may be larger than the area of one single to-be-colored sheet. The plurality of to-be-colored sheets are arranged aligning with the colored region and side by side in a direction perpendicular to the rubbing direction of the rubbing cloth. Moreover, the plurality of to-be-colored sheets are placed at different heights in a direction perpendicular to the surface of the base platform. After the rubbing cloth is colored by the one coloring sheet, the colored region of the rubbing cloth rolls over the plurality of to-be-colored sheets, and a pattern is formed on each of the to-be-colored sheets.

The rubbing cloth that is colored is used to perform rubbing alignment operation on the plurality of to-be-colored sheets placed at different heights, patterns with different indentation amounts may be obtained, so that the indentation amount of the rubbing cloth used to produce a most desired pattern may be determined according to the different patterns, so that subsequent process parameters can be adjusted.

In another implementation of the present embodiment, one coloring sheet and one to-be-colored sheet are provided, and the positions of the coloring sheet and the to-be-colored sheet align with each other. That is, the coloring sheet is placed between extension lines of two sides of the to-be-colored sheet along the rubbing direction of the rubbing cloth. The to-be-colored sheet and the coloring sheet may be rectangles, and the area of the to-be-colored sheet may be larger than the area of the coloring sheet, so that the region on the rubbing cloth which is colored by the coloring sheet may roll over the to-be-colored sheet and form a pattern on the to-be-colored sheet.

In another implementation of the present embodiment, a plurality of coloring sheets and a plurality of to-be-colored sheets are provided. In this case, the coloring sheets correspond to the to-be-colored sheets one by one. That is, each coloring sheet is placed between extending lines of two sides of a to-be-colored sheet placed at the same height as the coloring sheet along the rubbing direction of the rubbing cloth. The coloring sheets and the to-be-colored sheets may be rectangles, and the area of each to-be-colored sheet may be larger than the area of each coloring sheet, so that the region on the rubbing cloth which is colored by the coloring sheets may roll over the to-be-colored sheets and form patterns on the to-be-colored sheets. A height at which a to-be-colored sheet is placed in a direction perpendicular to the surface of the base platform is the same as the height at which a corresponding coloring sheet is placed in a direction perpendicular to the surface of the base platform.

The coloring sheet aligns with the to-be-colored sheet, so that after the rubbing cloth rolls on and rubs the coloring sheet, the rubbing cloth rolls on and rubs the to-be-colored sheet. Then, in one process of rolling and rubbing, the rubbing cloth may roll over the coloring sheet and the to-be-colored sheet successively, for detection of the rubbing cloth. Accordingly, the operation process may be simplified, and detection period may be shortened. In addition, the plurality of coloring sheets may be side by side in a direction perpendicular to the rubbing direction of the rubbing cloth, or may be spaced apart. Moreover, it is not necessary that the plurality of coloring sheets are arranged on one straight line. However, it should be avoided that coloring sheets overlap with each other in the rolling and rubbing direction of the rubbing roller, to ensure that only one coloring sheet roll over one region of the rubbing cloth. Moreover, the plurality of to-be-colored sheets may be side by side or be spaced apart in the direction perpendicular to the rubbing direction of the rubbing cloth.

It should be noted that, in order to make the detection result more accurate, in the embodiments as shown in FIGS. 2 and 3, prior to the steps S21 and S31, the method may also include: providing a substrate for detection on the base platform; and performing a preliminary rubbing process on the substrate for detection with the rubbing cloth.

The substrate for detection may be a substrate such as a bare glass or a glass coated with ITO (indium tin oxide) or the like, which is specifically used for a preliminary rubbing process of the rubbing cloth. The preliminary rubbing process refers to that after the rubbing cloth is attached on the rubbing roller, the rubbing roller rolls on and rubs the substrate for detection along the same direction for a preset number of times (for example for about 10 times) according to preset process parameters (such as a rotation speed of the rubbing roller, a traveling speed of the base platform and a rubbing depth). Orientations and bending states of the fluffs on the outer surface of the rubbing cloth in the preliminary rubbing process may be more approximate to the actual orientations and bending states in the rubbing alignment process, to further improve the accuracy of the detection.

It should be noted that, during the preliminary rubbing process, the area of the employed substrate for detection should be large enough to ensure that a region (that is a region for detection) other than the region for the rubbing alignment operation on the rubbing cloth is also subject to the preliminary rubbing process. Moreover, in order to ensure that the coloring sheet is easy to be placed, preferably, the substrate for detection may be removed after the preliminary rubbing process is completed.

In addition, in order to reduce the waste of the rubbing cloths, after the steps S23 and S34, the method may further include: performing a process of trimming on the unqualified friction cloth which has been detected, then returning to the steps S21 or S31. For disposal. For the rubbing cloth which is still unqualified after many times of trimming, it may be discarded.

A rubbing cloth which cannot be fixed may be directly discarded, while some unqualified rubbing cloths may be qualified after being trimmed. For example, when the surface of the rubbing cloth is attached with other fibers, after 2 to 3 times of trimming, the quality of the rubbing cloth may achieve the quality standard of the rubbing cloth and the trimmed rubbing cloth may be put into operation. This can reduce waste of rubbing cloths, and save production cost.

It should be noted that, for different production requirements, the quality requirements on the rubbing cloth may be different. According to the different patterns obtained in the detection process, the quality standard of the rubbing cloth may be divided into four categories: the first category, the pattern is colored uniformly and there is no line-shaped trace, it is the rubbing cloth with the best quality; the second category, there are 1 to 3 line-shaped traces in the pattern, and the width of the trace is less than 0.5 mm, it is the rubbing cloth with good quality; the third category, there more than 3 line-shaped traces in the pattern, and the width of the trace is less than 0.5 mm, it is the rubbing cloth with medium quality; and fourth, there are line-shaped traces in the pattern, and the width of the trace is larger than 0.5 mm, it is the rubbing cloth with bad quality. In the practical mass production, the rubbing cloth with better quality than the third category is considered as qualified. When the quality requirement of the product is higher, the standard for the qualification will be correspondingly raised to the second category, even to the first category. Therefore, the obtained pattern may be detected according to the above quality standard.

Figure 4:
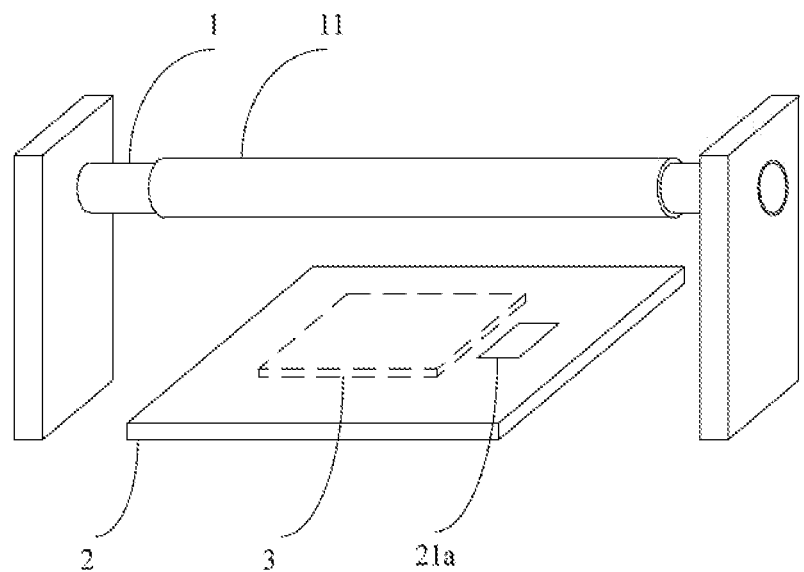
FIG. 4 illustrates a device for detecting a rubbing cloth provided by an embodiment of the present disclosure.

An embodiment of the present disclosure also provides a device for detecting a rubbing cloth. FIG. 4 illustrates a device for detecting a rubbing cloth provided by an embodiment of the present disclosure. As shown in FIG. 4, the device includes: a base platform 2, on which a coloring sheet 21a is provided; and a rubbing roller 1, configured to roll on the base platform 2. The outer surface of the rubbing roller 1 is provided with a rubbing cloth 11 which is to be detected, and the rubbing roller 1 is disposed parallel to the base platform 2.

In some embodiments, by coloring at least part of a region other than the region which will be used for a rubbing alignment operation on the rubbing cloth, it can prevent the pigment from contaminating the region where the substrate is located. Moreover, the rubbing cloth is detected according to the pattern of the colored region, and the quality of the rubbing cloth can be detected by observing the depth and the arrangement of the pattern. In these embodiments, the device for detecting a rubbing cloth may also be used as a device for producing an alignment film. The device may detect the rubbing cloth at the same time producing the alignment film.

Figure 5:
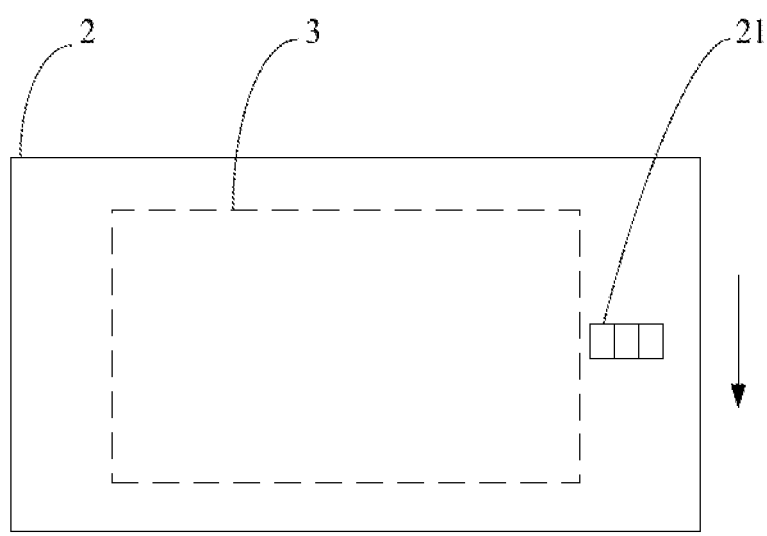
FIG. 5 is a top view of a base platform provided by an embodiment of the present disclosure.

FIG. 5 is a top view of a base platform provided by an embodiment of the present disclosure. The arrow direction in FIG. 5 is the movement direction of the rubbing roller with respect to the base platform. The device provided by the embodiment of the present disclosure also includes a first carrier sheet 21 disposed aligning with at least part of a region other than the region which will be used for a rubbing alignment operation on the rubbing cloth 11. The coloring sheet 21a is disposed on the first carrier sheet 21. During the operation process, the coloring sheet 21a is firstly placed on the first carrier sheet 21, and the first carrier sheet 21 is then placed on the base platform 2, which facilitates the transfer of the coloring sheet. Moreover, the thickness of the first carrier sheet 21 may match the thickness of the substrate 3 (the substrate is the substrate used for producing the alignment film). The thickness of the first carrier sheet 21 is adjusted to approximate the thickness of the substrate 3 in the practical production, to match the practical process. However, the indentation amount of the rubbing roller 1 when the most desired pattern is produced may be determined according to the detection result. For example, a plurality of first carrier sheets 21 are provided, while for the detection, only one of the first carrier sheets 21 is placed on the base platform 2 each time. For example, a first carrier sheet 21 with a thickness the same as that of the substrate 3 may be provided for a first time of detection; then a first carrier sheet 21 with a thickness 0.05 mm less than the thickness of the substrate 3 is provided for a second time of detection; and after that, a first carrier sheet 21 with a thickness 0.05 mm larger than the thickness of the substrate 3 is provided for a third time of detection. By comparing the patterns formed in the three times of detection, the optimal indentation amount of the rubbing roller is determined. Moreover, the first carrier sheet 21 is disposed other than of the region for bearing the substrate 3 on the base platform, and it can prevent the coloring sheet 21a from contaminating the rubbing cloth 11 corresponding to the substrate 3.

Preferably, as shown in FIG. 5, the device may include a plurality of first carrier sheets 21. The first carrier sheets 21 are side by side in a direction perpendicular to the rolling direction of the rubbing roller 1. The plurality of first carrier sheets 21 have different thicknesses, and are configured to bear the coloring sheet 21a. By providing a plurality of first carrier sheets 21 having different thicknesses, after the rubbing cloth 11 on the rubbing roller 1 rolls on the first carrier sheets 21 along the arrow direction in FIG. 5, the coloring sheets 21a placed on different first carrier sheets 21 may produce different patterns. By comparing the patterns produced on the different coloring sheets 21a, the indentation amount of the rubbing roller 1 when the most desired pattern is produced may be determined, for subsequent adjustment of process parameters. The height at which the coloring sheet 21a is placed may be adjusted by adjusting the thickness of the first carrier sheet 21. The thickness of the plurality of second carrier sheets 22 may differ from each other by 0.05 mm (for example, the thicknesses of the first carrier sheets 21 are 0.25 mm, 0.30 mm and 0.35 mm respectively), or may be 0.02 mm or other values.

It should be noted that, although there are only three first carrier sheets 21 shown in FIG. 5, in other embodiment, there may be provided with more or less first carrier sheet 21. In addition, the first carrier sheet 21 may be provided spaced apart. It is also not necessary that the plurality of first carrier sheets 21 are arranged in one straight line perpendicular to the rolling direction of the rubbing roller 1. However, it should ensure that one region on the rubbing cloth is colored only by one coloring sheet.

Figure 6:
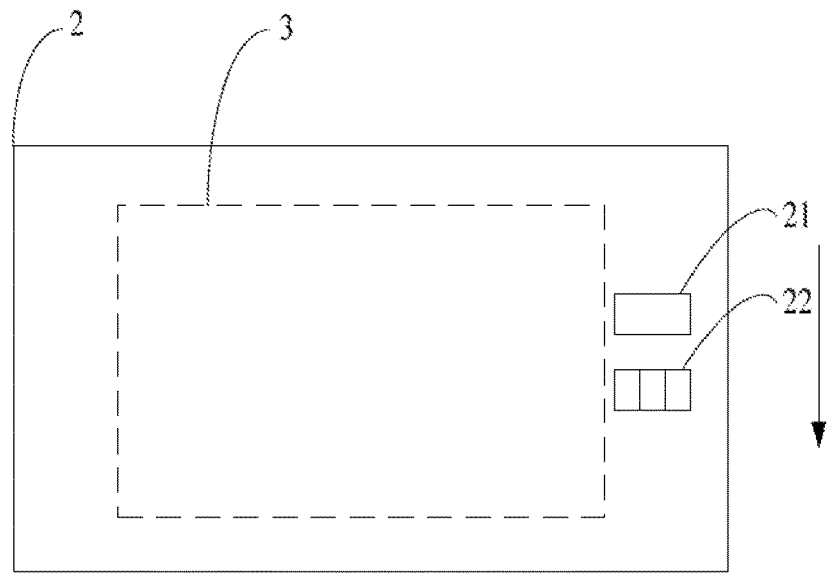
FIG. 6 is a top view of another base platform provided by an embodiment of the present disclosure.

FIG. 6 is a top view of another base platform provided by an embodiment of the present disclosure. As shown in FIG. 6, the device includes one first carrier sheet 21, and at the same time, also includes a second carrier sheet 22. The second carrier sheet 22 is configured to bear a to-be-colored sheet 22a, and is disposed on the base platform 2 and aligned with the first carrier sheet 21 in the rolling direction of the rubbing roller 1. By disposing the second carrier sheet 22 aligning with the first carrier sheet 21, after the rubbing roller 1 rolls over the coloring sheet 21a, the rubbing roller 1 may roll over the to-be-colored sheet 22a. Thereby, the rubbing roller may roll over the coloring sheet 21a and the to-be-colored sheet 22a successively with one rolling. Accordingly, the operation process may be simplified, and the detection period may be shortened.

Preferably, the device may also include a plurality of second bearing sheets 22. The plurality of second bearing sheets 22 are disposed on the base platform 2 aligning with the first bearing sheets 21 in the rolling direction of the rubbing roller 1, and the plurality of second bearing sheets 22 have different thicknesses. The arrow direction in FIG. 6 indicates the movement direction of the rubbing cloth with respect to the base platform, that is, the rolling direction of the rubbing roller 1. Firstly, the rubbing cloth 11 on the rubbing roller 1 is caused to roll over the coloring sheets 21a, and then roll over the to-be-colored sheets 22a which are placed at different heights, to obtain patterns corresponding to different indentation amounts. Therefore, the indentation amount of the rubbing cloth used to produce a most desired pattern may be determined according to the different patterns, so that subsequent process parameters can be adjusted. The height at which the coloring sheet 21a is placed may be adjusted by adjusting the thickness of the first carrier sheet 21, and the height at which the to-be-colored sheet 22a is placed may be adjusted by adjusting the thickness of the second carrier sheet 22. The thickness of the plurality of second carrier sheets 22 may differ from each other by 0.05 mm, and may be for example, 0.25 mm, 0.30 mm and 0.35 mm respectively. Of course, the difference between the second carrier sheets 22 may also be other values. However, it should ensure that the thickness of the second carrier sheet 22 is the same as the thickness of the corresponding first carrier sheet 21.

It should be noted that, when only one first carrier sheet and one second carrier sheet are provided, the first carrier sheet is disposed between extending lines of the two sides of the second carrier sheet along the rolling direction of the rubbing roller, such that the second carrier sheet will roll over all of the regions of the first carrier sheet over which the rubbing roller has rolled. When one first carrier sheet and a plurality of second carrier sheets are provided, the first carrier sheet is disposed between extending lines of two sides of the plurality of second carrier sheets, which are spaced apart by a farthest distance in a direction perpendicular to the rolling direction of the rubbing roller, such that the second carrier sheet will roll over all of the regions of the first carrier sheet over which the rubbing roller has rolled.

It should be noted that, although there are only three second carrier sheets shown in FIG. 6, in other embodiment, there may be provided more or less second carrier sheets. In addition, the second carrier sheets 22 may be disposed spaced apart. It is also not necessary that the plurality of second carrier sheets are placed in one straight line perpendicular to the rubbing alignment operation direction. However, it should be ensured that a pattern can be formed on each second carrier sheet 22 after the rubbing roller 1 has rolled over.

Figure 7:
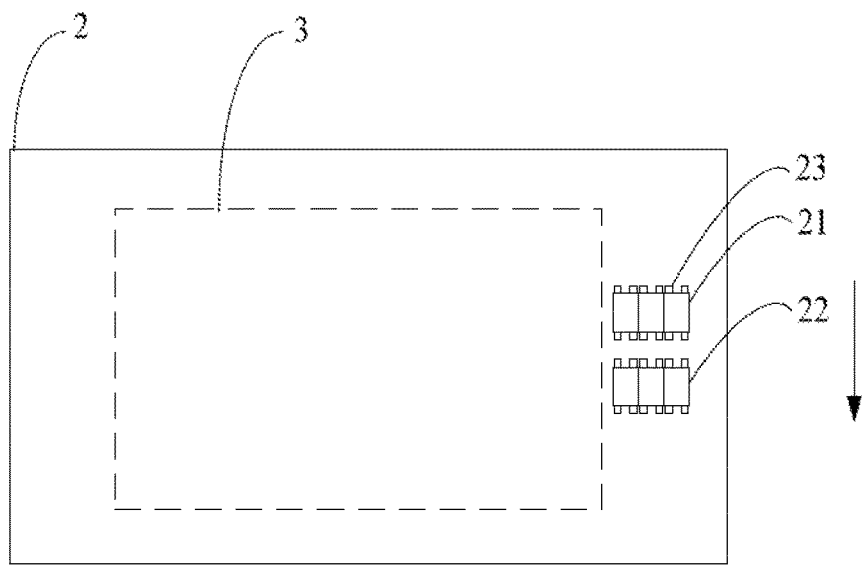
FIG. 7 is a top view of another base platform provided by an embodiment of the present disclosure.

FIG. 7 is a top view of another base platform provided by an embodiment of the present disclosure. The arrow direction in FIG. 7 indicates the movement direction of the rubbing roller with respect to the base platform. As shown in FIG. 7, the device includes a plurality of first carrier sheets 21 disposed side by side in a direction perpendicular to the rolling direction of the rubbing roller 1. The plurality of first carrier sheets 21 have different thicknesses, and are configured to bear the coloring sheets 21a.

It should be noted that, the first carrier sheets 21 may be disposed spaced apart. It is also not necessary that the first carrier sheets 21 are disposed at the same straight line perpendicular to the rolling direction of the rubbing roller 1. However, it should be ensured that one region on the rubbing cloth can be colored by only one coloring sheet 21a.

The device also includes a plurality of second carrier sheets 22 configured to bear to-be-colored sheets 22a. The second carrier sheets 22 are disposed on the base platform 2 corresponding to the first carrier sheets 21 one by one in the rolling direction of the rubbing roller 1, and the thickness of the second carrier sheet 22 is the same as the thickness of the corresponding first carrier sheet 21. Each first carrier sheet is disposed between extending lines of two sides of the second carrier sheet disposed at the same height along the rolling direction of the rubbing roller, such that the corresponding second carrier sheet will roll over all of the regions of the first carrier sheet over which the rubbing roller has rolled. The arrow direction in FIG. 7 indicates the movement direction of the rubbing cloth with respect to the base platform. The second carrier sheet 22 is disposed corresponding to the first carrier sheet 21, such that after the rubbing cloth 11 on the rubbing roller 1 rolls over the coloring sheet 21a, the rubbing cloth 11 continues to roll over the to-be-colored sheet 22a. Therefore, the rubbing cloth may roll over the coloring sheet 21a and the to-be-colored sheet 22a successively with one rolling. Accordingly, the operation process may be simplified, and the detection period may be shortened. Moreover, the indentation amount of the rubbing cloth used to produce a most desired pattern may be determined according to the patterns on the to-be-colored sheets disposed at different heights, for subsequent adjustment of process parameters.

Preferably, as shown in FIG. 7, a stopper structure 23 is provided on the base platform 2 to limit the positions of the first carrier sheet 21 and the second carrier sheet 22. The stopper structure 23 may be a raised block or a stopper hole provided in the base platform 2. When a stopper hole is provided on the base platform 2, correspondingly, a stopper protrusion can be inserting into the stopper hole is disposed on the first carrier sheet 21 and the second carrier sheet 22. By providing the stopper structure 23, it can avoid displacements of the first carrier sheet 21 and the second carrier sheet 22 during the rubbing alignment operation.

Below, the operation process of the device for detecting a rubbing cloth provided by the embodiments of the present disclosure will be briefly described.

Firstly, the rubbing cloth is adhered on the rubbing roller with double-sided adhesive, and the rubbing roller is suspended in the detection device.

Secondly, a substrate is provided on the base platform for performing a preliminary rubbing process, and process parameters (such as rotation speed of the rubbing roller, the traveling speed of the base platform and a rubbing depth) of the detection device are set up.

Then, the rubbing roller rolls and rubs for a preset number of times (for example, for 10 times) along the same direction on the substrate.

After that, the substrate is removed, and a first carrier sheet bearing a coloring sheet is placed on the base platform, and is positioned by the stopper structure. Then, the detection device is started, and the rubbing roller rolls over the coloring sheet.

Finally, the detection device is shut down, and the coloring sheet is removed.

It should be noted that, when there is provided a second carrier sheet, the first carrier sheet bearing the coloring sheet and the second carrier sheet bearing the to-be-colored she may be respectively placed on the base platform and positioned by the corresponding stopper structure. Then, the detection device is started, to cause the rubbing roller to roll over the coloring sheet, and after that, the rubbing roller continues to roll over the to-be-colored sheet. Finally, the to-be-colored sheet is removed.

Figure 8:
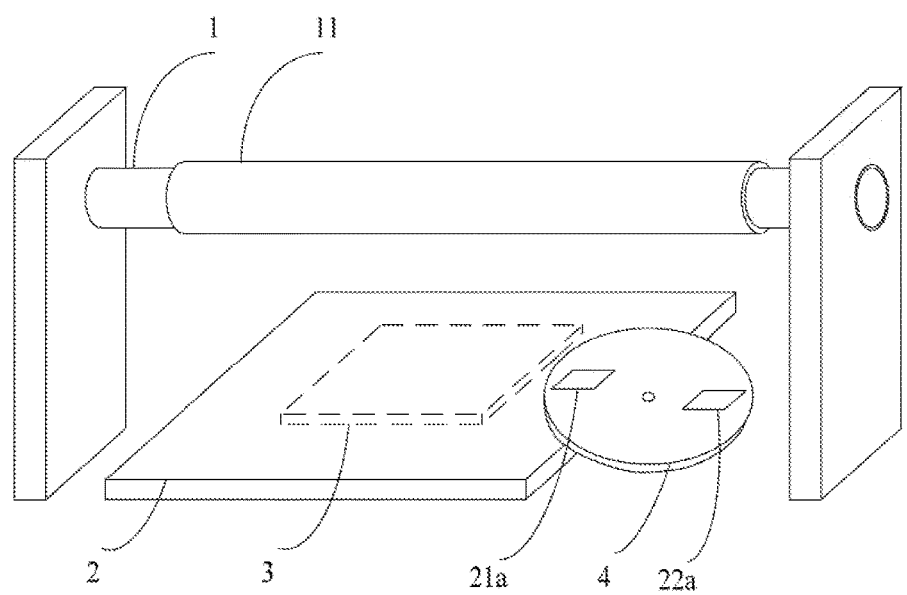
FIG. 8 illustrates another device for detecting a rubbing cloth provided by an embodiment of the present disclosure.

FIG. 8 illustrates another device for detecting a rubbing cloth provided by an embodiment of the present disclosure. As shown in FIG. 8, the device also includes a rotary disk 4 rotatably provided on the base platform 2. The coloring sheet 21a and the to-be-colored sheet 22a are provided on the rotary disk 4. The coloring sheet 21a and the to-be-colored sheet 22a are spaced apart along the circumferential direction of the rotary disk 4. The rotary disk 4 may be rotated around the rotary shaft of the rotary disk 4 by a stepping motor, to move the coloring sheet 21a and the to-be-colored sheet 22a, such that after the rubbing roller 1 rolls over the coloring sheet 21a, before the rubbing roller 1 rolls over for the second time, the rotary disc is rotated by the stepping motor, to bring the to-be-colored sheet 22a to the position where the coloring sheet 21a was located. Then, the rubbing roller 1 will roll over the to-be-colored sheet 22a to form a pattern on the to-be-colored sheet 22a, achieving automation of the detection process.

It should be noted that, in the embodiments of the present disclosure, the length of each of the coloring sheets and the to-be-colored sheets along the rubbing alignment operation should be equal to an integral multiple of the circumference of the cylinder formed by the rubbing cloth on the rubbing roller, to ensure that the entire outer surface of the rubbing cloth can be detected, thus improving the accuracy of the detection. Moreover, after the rubbing cloth is provided on the rubbing roller, the preliminary rubbing process should be performed on the substrate for about 10 times. That is, after the rubbing cloth is provided on the rubbing roller, the rubbing roller rolls and rubs on the substrate along the same direction for about 10 times and the distance between the rubbing roller and the substrate remains constant, such that orientations and bending states of the fluffs of the outer surface of the rubbing cloth in the preliminary rubbing process may be more approximate to the actual orientations and bending states in the rubbing alignment process, to further improve the accuracy of the detection.

In addition, the rubbing roller and the base platform may be just the processing device for the rubbing alignment process. Of course, it is also possible to separately manufacture a dedicated rubbing roller and a base platform. Further, the region other than of the substrate corresponding to the rubbing cloth may be cut off to be disposed on the detection device and used for detection.

Below, the operation process of the device for detecting a rubbing cloth provided by the embodiments of the present disclosure as shown in FIG. 8 will be briefly described.

Firstly, the rubbing cloth is adhered on the rubbing roller with double-sided adhesive, and the rubbing roller is suspended in the detection device.

Secondly, a substrate is provided on the base platform for performing a preliminary rubbing process, and process parameters (such as rotation speed of the rubbing roller, a traveling speed of the base platform and a rubbing depth) of the detection device are set up.

Then, the rubbing roller rolls and rubs for a preset number of times (for example, for 10 times) along the same direction on the substrate.

After that, a rotary disc bearing a coloring sheet and a to-be-colored sheet is placed on the base platform, the position of the rotary disc is adjusted, such that the coloring sheet corresponds to at least part of the region other than the region for the rubbing alignment operation on the rubbing cloth. Then, the detection device is started, and the rubbing roller rolls over the coloring sheet.

Subsequently, after the rubbing roller rolls over the coloring sheet, the rotary disc is rotated, such that the to-be-colored sheet is in the position where the coloring sheet was previously located, and then, the rubbing roller is caused to roll over the to-be-colored sheet.

Finally, the detection device is shut down, and the to-be-colored sheet is removed.

The foregoing is only preferred embodiments of the present disclosure, and is not intended to limit the present disclosure. Any modification, equivalent substitution, improvement, and the like within the spirit and principles of the present disclosure should be encompassed by the protective scope of the present disclosure.

What is claimed is:

1. A method for detecting a rubbing cloth, comprising:
   rubbing a coloring sheet with the rubbing cloth to color the rubbing cloth;
   rubbing a to-be-colored sheet at a rubbed region with the rubbing cloth after the rubbing cloth is colored; and
   detecting the rubbing cloth by detecting a pattern formed in the rubbed region of the to-be-colored sheet after the to-be-colored sheet is rubbed by the rubbing cloth.

2. The method for detecting a rubbing cloth according to claim 1, wherein the coloring sheet is rubbed with at least part of the region other than a region for rubbing alignment operation on the rubbing cloth.

3. The method for detecting a rubbing cloth according to claim 1, wherein the step of rubbing a coloring sheet with the rubbing cloth comprises:
   providing a coloring sheet on a base platform;
   attaching the rubbing cloth on a rubbing roller; and
   rubbing the coloring sheet with a rolling action of the rubbing roller.

4. The method for detecting a rubbing cloth according to claim 3, wherein the step of rubbing the coloring sheet with a rolling action of the rubbing roller comprises:
   rubbing a plurality of coloring sheets with the rubbing cloth;
   wherein the plurality of coloring sheets are disposed side by side along a direction perpendicular to a rubbing direction of the rubbing cloth, and the plurality of coloring sheets are disposed at different heights in a direction perpendicular to a surface of the base platform.

5. The method for detecting a rubbing cloth according to claim 3, wherein prior to the step of rubbing the coloring sheet with a rolling action of the rubbing roller, the method also comprises:
   providing a substrate for detection on the base platform; and
   perform a preliminary rubbing process on the substrate for detection with the rubbing cloth.

6. The method for detecting a rubbing cloth according to claim 1, wherein the step of rubbing a to-be-colored sheet at a rubbed region with the rubbing cloth after the rubbing cloth is colored comprises:
   providing the to-be-colored sheet at downstream of the coloring sheet along a rubbing direction of the rubbing cloth; and
   immediately after the coloring sheet is rubbed with the rubbing cloth, rubbing the to-be-colored sheet.

7. The method for detecting a rubbing cloth according to claim 6, wherein
   the step of providing the to-be-colored sheet at downstream of the coloring sheet along a rubbing direction of the rubbing cloth comprises: a plurality of to-be-colored sheets are disposed side by side in the direction perpendicular to the rubbing direction of the rubbing cloth, wherein the plurality of to-be-colored sheets are disposed at different heights in the direction perpendicular to a surface of the base platform.

8. The method for detecting a rubbing cloth according to claim 7, wherein the plurality of to-be-colored sheets are disposed corresponding to the plurality of coloring sheets one by one, and a pair of corresponding to-be-colored sheet and coloring sheet are disposed at the same height.

9. The method for detecting a rubbing cloth according to claim 4, wherein a plurality of carrier sheets with different thicknesses are employed to bear the coloring sheets, to dispose the plurality of coloring sheets at different heights.

10. The method for detecting a rubbing cloth according to claim 7, wherein a plurality of carrier sheets with different thicknesses are employed to bear the coloring sheets and the to-be-colored sheets, to dispose the plurality of coloring sheets at different heights.

11. A device for detecting a rubbing cloth, comprising:
    a base platform, wherein a coloring sheet is provided on the base platform;
    a rubbing roller, wherein the rubbing cloth to be detected is provided on an outer surface of the rubbing roller, the rubbing roller is disposed in parallel to the base platform and the rubbing roller is configured to rub the coloring sheet; and
    a to-be-colored sheet, disposed on the base platform, and subject to being rubbed by the rubbing cloth after the rubbing cloth is colored by the coloring sheet,
    wherein the rubbing cloth is detected by detecting a pattern formed on the to-be-colored sheet after the to-be-colored sheet is rubbed by the rubbing cloth.

12. The device for detecting a rubbing cloth according to claim 11 further comprising a first carrier sheet disposed corresponding to at least part of the region other than the region for rubbing alignment operation on the rubbing cloth, and the coloring sheet is disposed on the first carrier sheet.

13. The device for detecting a rubbing cloth according to claim 12 further comprising a plurality of said first carrier sheets, the plurality of said first carrier sheets are side by side in a direction perpendicular to a rubbing direction of the rubbing cloth, and the plurality of said first carrier sheets have different thicknesses, and the plurality of said first carrier sheets are configured to bear the coloring sheets respectively.

14. The device for detecting a rubbing cloth according to claim 11, wherein the to-be-colored sheet is disposed at downstream of the coloring sheet along a rubbing direction of the rubbing cloth.

15. The device for detecting a rubbing cloth according to claim 13 further comprising a plurality of second carrier sheets configured to bear the to-be-colored sheets, the plurality of second carrier sheets are disposed at downstream of the first carrier sheets along the rubbing direction of the rubbing cloth, and corresponding to the plurality of first carrier sheets one by one, and a pair of corresponding first carrier sheet and second carrier sheet have same thickness.

16. The device for detecting a rubbing cloth according to claim 15, wherein a stopper structure is provided on the base plat form and configured to limit positions of the first carrier sheets and the second carrier sheets.

17. The device for detecting a rubbing cloth according to claim 11 further comprising a rotary disc rotatably provided on the base platform, wherein the coloring sheet and the to-be-colored sheet are disposed on the rotary disc, and the coloring sheet and the to-be-colored sheet are spaced apart along circumferential direction of the rotary disc.

18. A device for manufacturing an alignment film, comprising:
- a base platform; and
- a rubbing roller, wherein a rubbing cloth is provided on an outer surface of the rubbing roller, the rubbing roller is disposed in parallel to the base platform, wherein
- a processing region configured to position a substrate with a film to be processed and a detection region configured to detect the rubbing cloth are provided on the base platform, wherein a coloring sheet and a to-be-colored sheet are placed on the detection region; and
- the rubbing roller is configured to rub the coloring sheet while processing the substrate with a film to be processed.

* * * * *